United States Patent
Owen et al.

(10) Patent No.: US 7,189,574 B2
(45) Date of Patent: Mar. 13, 2007

(54) MEASUREMENT OF NITROGEN CONTENT IN A GAS MIXTURE BY TRANSFORMING THE NITROGEN INTO A SUBSTANCE DETECTABLE WITH NONDISPERSIVE INFRARED DETECTION

(75) Inventors: Thomas E. Owen, Helotes, TX (US); Michael A. Miller, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/810,103

(22) Filed: Mar. 26, 2004

(65) Prior Publication Data

US 2004/0225455 A1 Nov. 11, 2004

Related U.S. Application Data

(60) Provisional application No. 60/457,906, filed on Mar. 27, 2003.

(51) Int. Cl.
*G01N 31/00* (2006.01)

(52) U.S. Cl. ............... 436/106; 436/110; 436/111; 436/113; 436/114

(58) Field of Classification Search ........... 436/164, 436/106, 113, 114, 115, 124, 139, 143, 144, 436/111, 110
See application file for complete search history.

(56) References Cited

U.S. PATENT DOCUMENTS

| | | | | |
|---|---|---|---|---|
| 2,166,611 A | * | 7/1939 | Shapleigh | 423/362 |
| 2,894,821 A | * | 7/1959 | Jordan et al. | 423/362 |
| 3,616,273 A | * | 10/1971 | Oita | 205/780.5 |
| 4,390,785 A | * | 6/1983 | Faulhaber et al. | 250/330 |
| 5,711,147 A | * | 1/1998 | Vogtlin et al. | 60/274 |
| 6,244,097 B1 | | 6/2001 | Schley et al. | 73/23.2 |
| 6,446,487 B1 | | 9/2002 | Van Wesenbeeck et al. | 73/23.2 |
| 2002/0040590 A1 | | 4/2002 | Schley | 73/23.2 |

OTHER PUBLICATIONS

PCT International Search Report, PCT /US04/09107, 16 pgs.

* cited by examiner

*Primary Examiner*—Jill Warden
*Assistant Examiner*—Sam P. Siefke
(74) *Attorney, Agent, or Firm*—Baker Botts L.L.P.

(57) ABSTRACT

A method of determining the amount of nitrogen in a gas mixture. The constituent gases of the mixture are dissociated and transformed to create a substance that may measured using nondispersive infrared adsorption techniques.

11 Claims, 6 Drawing Sheets

| GAS COMPONENT (DISSOCIATION) | MOLE % | COMPUTATION PATH | IONIZATION POTENTIAL (eV) | CHEMICAL BOND STRENGTH (kj/mol) |
|---|---|---|---|---|
| 1-BUTANE AND $C_5+$ | 0.50 | $C_4H_{10} + \bar{e} \rightarrow C_4H_9^+ + H\circ + 2\bar{e}$ | 10.57 | 411.1 |
| PROPANE | 0.80 | $C_3H_8 + \bar{e} \rightarrow C_3H_7^+ + H\circ + 2\bar{e}$ | 10.95 | 413.0 |
| ETHANE | 1.50 | $C_2H_6 + \bar{e} \rightarrow C_2H_5^+ + H\circ + 2\bar{e}$ | 11.52 | 422.8 |
| METHANE | 95.00 | $CH_4 + \bar{e} \rightarrow CH_3^+ + H\circ + 2\bar{e}$ | 12.51 | 438.5 |
| DILUENT CARBON DIOXIDE | 1.30 | $CO_2 + \bar{e} \rightarrow CO^+ + O + 2\bar{e}$ | 13.773 | 532.2 |
| DILUENT NITROGEN | 1.00 | $N_2 + \bar{e} \rightarrow N^+ + N + 2\bar{e}$ | 15.581 | 945.3 |
| METHYL ($CH_3//CH_4$) | | $CH_3^+ + \bar{e} \rightarrow CH^{2+} + H\circ + 2\bar{e}$ | 9.84 | 1095.0 |

| GAS COMPONENT (ASSOCIATION) | MOLE % | COMPUTATION PATH | ENTHALPY OF FORMATION (kj/mol) | REQUIRED SOURCE COMPONENT |
|---|---|---|---|---|
| 2-BUTANOL | 0.4 | $3CH_3\circ + H\circ + O \rightarrow C_3H_{10}O$ | 658 | $CO_2$ |
| ETHANOL | 0.3 | $2CH_3\circ + O \rightarrow C_2H_6O$ | 776 | $CO_2$ |
| ETHANOL | 0.3 | $C_2H_6 + O \rightarrow C_2H_6O$ | 776 | $CO_2$ |
| METHANOL | 0.3 | $CH_4 + O \rightarrow CH_4O$ | 845 | $CO_2$ |
| AMMONIA | 2.0 | $N + 3H\circ \rightarrow NH_3$ | 934 | $N_2$ |
| ETHANE | 5.7 | $2CH_3\circ \rightarrow C_2H_6$ | 1027 | $CH_4$ |
| METHANE | 91.0 | $CH_3\circ + H\circ \rightarrow CH_4$ | 1133 | $CH_4$ |
| 2-BUTANOL | | $H\circ + O \rightarrow HO\circ$ | 1293 | $CO_2$ |
| HYDROXYL | | $CH_3\circ + HO\circ \rightarrow CH_4O$ | 845 | $CO_2$ |
| METHANOL | | $3CH_2\circ + H\circ + HO\circ \rightarrow C_3H_8O$ | 704 | $CH_3/CO_2$ |
| 2-PROPANOL | | $4CH_3\circ + 2H\circ + O \rightarrow C_4H_{10}O$ | 658 | $CH_3/CO_2$ |

MEASUREMENT OF NITROGEN CONTENT IN A GAS MIXTURE BY TRANSFORMING THE NITROGEN INTO A SUBSTANCE DETECTABLE WITH NONDISPERSIVE INFRARED DETECTION

RELATED PATENT APPLICATION

This application claims the benefit of U.S. Provisional Application No. 60/457,906, filed Mar. 27, 2003 and entitled "Measurement of Diluent (Nitrogen) Gas Content in a Natural Gas by Reforming the Gas".

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

TECHNICAL FIELD OF THE INVENTION

This invention relates to methods and systems for measuring the diluent concentrations in a gas mixture, and in particular, for measuring the nitrogen concentration in the gas.

BACKGROUND OF THE INVENTION

Knowledge of diluent gas components and their concentrations in natural gas is of significant importance to the handling, transmission, and custody transfer of the gas. This knowledge is of primary importance with respect to processed natural gas transmitted and distributed nationwide for sale and consumption. It is also important with respect to natural gas in its raw form recovered at the wellhead (production gas) to identify the gas composition entering the processing plant and to account accurately for custody transfer pricing between gas industry producers and processors. The resulting processed gas, properly adjusted to a normal range of acceptable commercial composition, enters a network of gas transmission trunk pipelines that bring together several independent sources of processed gas from different geographical regions and thereafter that gas is distributed via smaller and more numerous pipelines to municipal, industrial, and residential consumers. At many points in this gas transport and transfer network, custody transfer between owners and customers occurs wherein the thermal energy content and quality of the gas must be determined in order to set the selling price and to establish that the transported gas mixture is in compliance with regulatory standards. These requirements are of major importance to the economics and business enterprise within the gas industry. Therefore, as natural gas industry transport and custody transfer operations expand, more efficient and more widely distributed capabilities are needed for monitoring the gas energy content and diluent gas components in processed natural gas. In particular, these monitoring techniques must be accurate, reliable, safe, and capable of near-real-time operation as well as inexpensive enough for cost-effective widespread installation and use.

One present-day method used for determining the heating value (thermal energy content) of processed natural gas employs a natural gas chromatograph instrument to measure the various hydrocarbon constituents and diluent gas constituents, wherein the latter are primarily carbon dioxide and molecular nitrogen. The diluent gases are typically present in amounts of only a few percent by volume and are required to be less than a total concentration of six percent by federal regulatory limit. Gas analysis data from the gas chromatograph are used to calculate the heating value of the gas using established thermodynamic relationships. However, the cost of gas chromatograph installations and their operation is sufficiently high that their widespread use is prohibitive.

Other methods for assessing natural gas energy content are in various stages of research and development. Some of these methods are "inferential" and are aimed at measuring certain inherent thermodynamic and physical properties of the gas which, by correlative analysis, can be collectively interpreted to yield an accurate and unambiguous value of the gas heating value. One such method has recently been demonstrated to yield gas energy measurements to within the same accuracy generally attributed to gas chromatograph determinations. This inferential method requires input information on the pressure, temperature, speed of sound, carbon dioxide concentration, and molecular nitrogen concentration in the gas in order to determine the thermal heating value. This method is described in U.S. Pat. No. 6,604,051 B1, entitled "System and Method to Determine Thermophysical Properties of a Multi-Component Gas" and U.S. Pat. No. 6,704,660 entitled "A System and Method to Determine Thermophysical Properties of a Multi-Component Gas at Arbitrary Temperature and Pressure", both to K. Behring and T. Morrow.

Present-day sensor technology is available for directly measuring the pressure, temperature, speed of sound, and carbon dioxide parameters needed for the energy analysis. However, because of its stable chemical nature, there are no existing methods for directly sensing molecular nitrogen. Consequently, to fully implement the inferential method of natural gas energy determination, a means for determining the molecular nitrogen diluent content is required.

DETAILED DESCRIPTION OF THE INVENTION

The invention disclosed herein pertains to methods for determining the amount of nitrogen in successive samples of a gas mixture. The methods are "two-step" methods that each provides a near-real-time means for determining the nitrogen diluent gas content of the gas. The methods are particularly useful for natural gas mixtures, and are described herein in that context, but the methods may be applied to other gas mixtures as well.

As explained below, the methods comprise a first step of transforming the nitrogen in the gas such that it may be detected by nondispersive infrared detection. In the following description, two examples of such a first step are described: applying a chemical reforming process to the gas to produce gaseous ammonia or, alternatively, using direct excitation-dissociation-formation processes to generate nitrogen molecular ions. The second step is using infrared detection to sense the reformed ammonia product, or infrared-active molecular ions of nitrogen, to infer and determine the original nitrogen content of the gas.

Chemically Reforming the Gas to Create Ammonia

In a first embodiment, the first step is a chemical reforming process. In chemical reforming, the composition of the natural gas, using only its self-contained constituents, is transformed, in part, to other compounds that are formed by dissociating and combining the constitutive elements of the original gas. In particular, the molecular nitrogen ($N_2$) is reformed to produce ammonia ($NH_3$) by dissociating and associating part or all of the nitrogen with hydrogen derived from dissociating the abundant amount of methane ($CH_4$) in the gas. The second step is a quantitative measurement of the ammonia produced by the reforming process from which the original nitrogen content of the natural gas may be determined.

Reforming the natural gas is accomplished by adding a sufficient amount of energy to cause chemical bonds between the carbon and hydrogen atoms of one or more of the hydrocarbon gas constituents and the nitrogen atoms of the molecular nitrogen diluent gas to dissociate. This dissociation makes the atoms free to re-associate to form other chemical compounds and, in part, to recombine to form new fractional amounts of the same compounds that were originally present in the gas. A preferred result and an object of controlling the dissociation energy introduced into the gas is to promote the recombination of all or a large proportion of the dissociated nitrogen content with the hydrogen dissociated from methane and other hydrocarbons to form gaseous ammonia. The remaining carbon and hydrogen atoms are reformed into revised fractional amounts of hydrocarbon gases common to the original natural gas.

As stated in the preceding paragraph, chemical dissociation applies primarily to the abundant methane hydrocarbon component ($CH_4$) and to the molecular nitrogen diluent gas component ($N_2$) such that, as the added energy is absorbed, a significant part of the nitrogen is reformed, i.e., reacted with hydrogen, to produce gaseous ammonia ($NH_3$). The added energy may be readily introduced either as a thermalizing electrical arc in which essentially all of the chemical bonds of the gas molecules within the arc are fully dissociated. Alternatively, a nonthermal plasma discharge of limited and controlled energy may be used, whereby only those bonds are dissociated for which the energy thresholds are exceeded. Both of these energy-injecting methods are different from outright combustion of the gas because no oxidant is present in the gas to support the combustion process. Other methods are also potentially applicable for natural gas reforming, including, in particular, catalytic methods capable of stimulating selective reactions among the various constituents of the gas to form new compounds.

By introducing sufficient energy into the gas, the affinity of nitrogen and hydrogen to form ammonia may be used advantageously to produce ammonia as a desired product of the reforming process. This nitrogen-based compound may then be sensed directly and quantitatively measured by a nondispersive infrared optical radiation absorption technique similar to that commonly used to measure other trace gases in air and other gas mixtures. With specific regard to ammonia measurements in natural gas, ammonia has two narrow optical absorption bands at wavelengths of 10.34 µm and 10.74 µm in the infrared range where no interfering infrared absorption bands associated with the natural gas constituents exist.

The gas reforming process underlying one embodiment of this invention may be considered to take place in a plasma chemistry reactor through which samples of natural gas flow, and are reformed to contain measurable amounts of ammonia. The most probable reaction pathways for such a plasma discharge reactor may be postulated on the basis of the energies of dissociation and reassociation beginning with the active species most likely to be initiated and progressing through reactions requiring increasing amounts of excitation energy. Although the chemical kinetics of the plasma-induced reactions are complex and the resulting reaction paths are only approximately predictable by energy considerations alone, such energy-based estimates provide a practical first-order approach to characterizing the desired natural gas reforming process.

Figure 1:
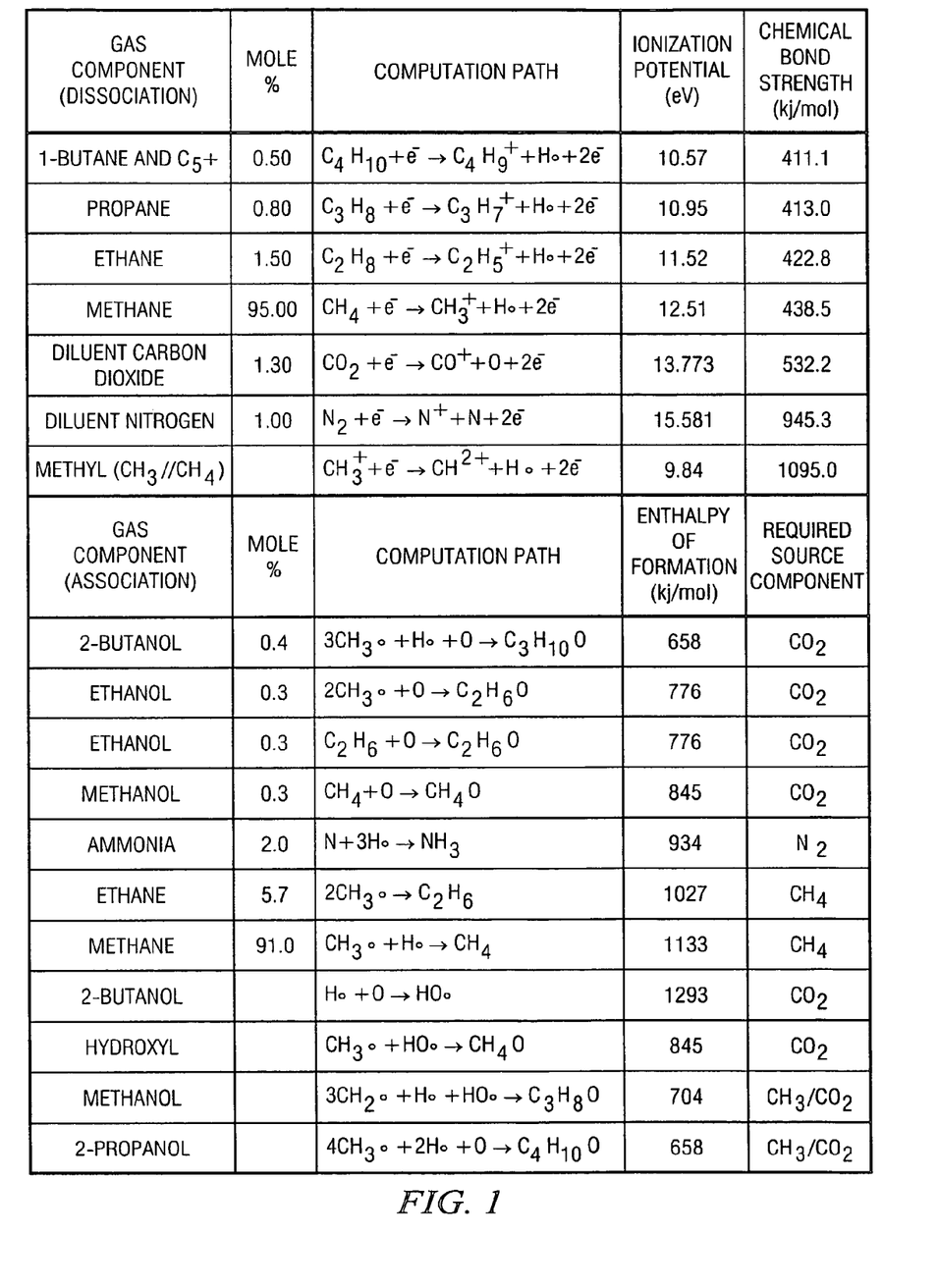
FIG. 1 is a table of the potential dissociation and reassociation paths for ionization and reforming of an example natural gas.

FIG. 1 lists, for an example natural gas mixture, the potential dissociation and reassociation pathways in ascending order of ionization potential and enthalpy of formation, respectively. The example natural gas mixture has a broadly typical composition characterized by:

| | |
|---|---|
| Methane ($CH_4$): | 95.0 mole % |
| Ethane ($C_2H_6$) | 1.5 mole % |
| Carbon Dioxide ($CO_2$): | 1.3 mole % |
| Nitrogen ($N_2$): | 1.0 mole % |
| Propane ($C_3H_8$): | 0.8 mole % |
| i-Butane ($C_4H_{10}$) and $C_5$+: | 0.5 mole % |

For the desired reforming reaction that produces ammonia, the plasma discharge energy must be sufficiently high to dissociate the molecular nitrogen diluent gas having a concentration of typically 1.0 mole % in the natural gas. The ionization potentials in FIG. 1 indicate that, with the exception of secondary ionizations and dissociations such as methyl, dissociation of the molecular nitrogen component requires more energy of dissociation than any other constituent in the original natural gas. Thus, if the nitrogen is excited to dissociation, all of the input gas constituents will be dissociated. In practice, the nonthermal plasma discharge may be made sufficiently energetic to dissociate the entire composition of the input gas through the molecular nitrogen component but also may be restricted in its energy to prevent the formation of higher-order dissociations such as the methyl radical component shown in FIG. 1. In contrast, if thermalizing plasma discharges (electrical arcs) are allowed, all of the dissociations listed in FIG. 1 (and more) will occur. Therefore, certain advantages may be gained by using nonthermal plasma discharges to achieve better energy control.

From the reassociation reactions listed in FIG. 1, the lowest energy reforming reactions (partial oxidations) are dependent on oxygen sourced from the dissociated carbon dioxide in the original gas. The alcohols that result from this minor source of oxygen are relatively small in concentration and essentially negligible in the reformed gas products. Ammonia is the next most sensitive reforming reaction and is the desired target transformation product of the process. The two most predominant reforming reactions are the conversion of dissociated methane to ethane followed by dissociated methane recombining to methane. In practice, the several reforming reactions described above are expected to dominate the reforming process for both nonthermal and thermalizing plasma discharge excitations although the minor presence of oxygen derived from the carbon dioxide diluent might also introduce some relatively negligible hydroxyl reactions.

FIG. 1 further presents a number of preliminary estimates of the reformed gas concentrations based on the assumption of complete volumetric ionization and dissociation of the input gas sample at least to a level exceeding the threshold for dissociating molecular nitrogen. On this basis, if a large majority of the nitrogen in the input gas is reformed, the resulting ammonia content will be in the range of 1–2 mol % in the reformed gas mixture.

Thorough volumetric ionization and dissociation of the input gas is essential for producing the maximum practical amount of ammonia. Moreover, the volumetric ionization process must be consistent from sample to sample of the input gas in order to yield accurately scaled quantitative determinations of the original molecular nitrogen in the natural gas.

Figure 2:
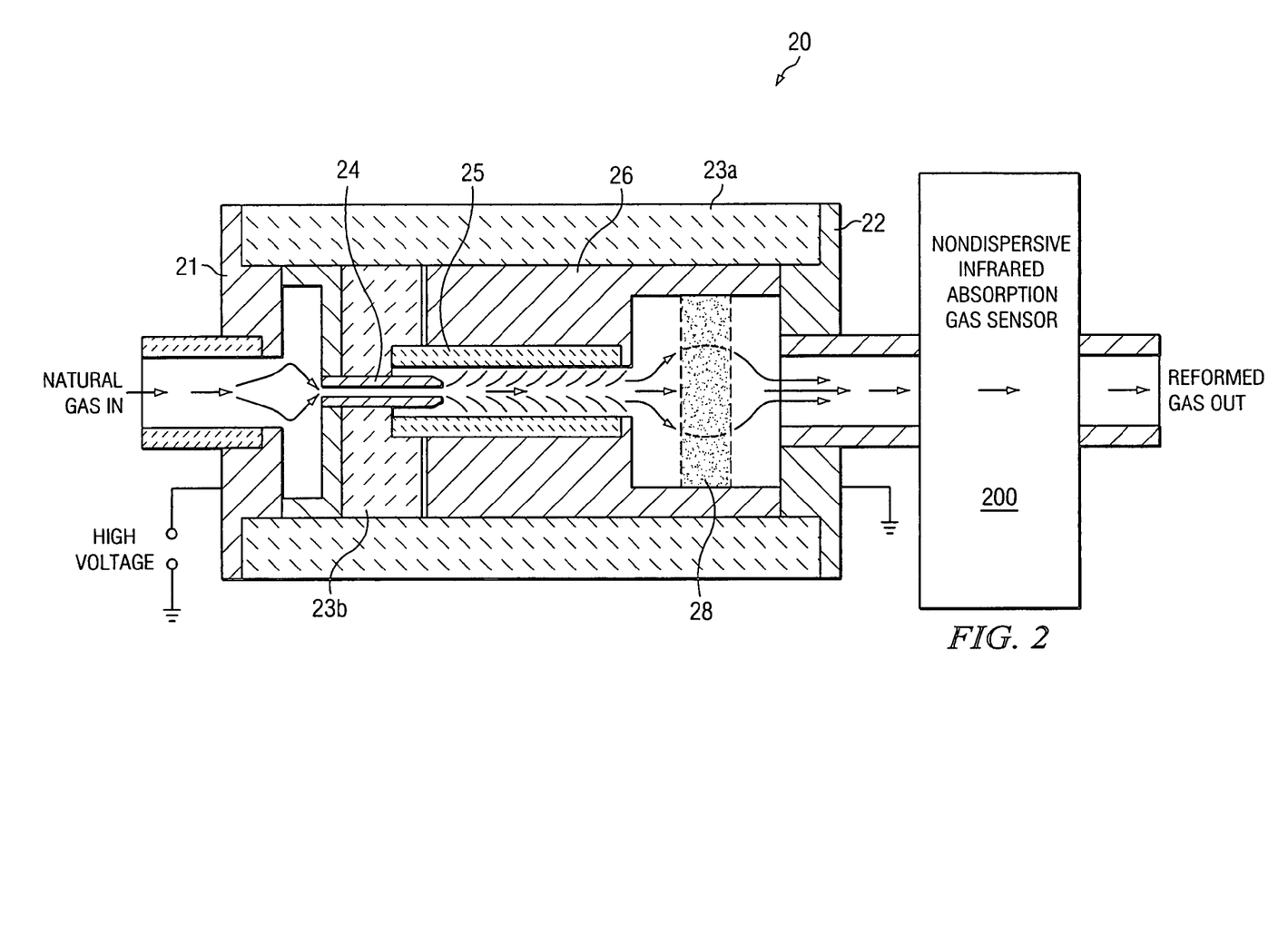
FIG. 2 illustrates a first embodiment of a nonthermal plasma gas reforming chamber.
Figure 3A:
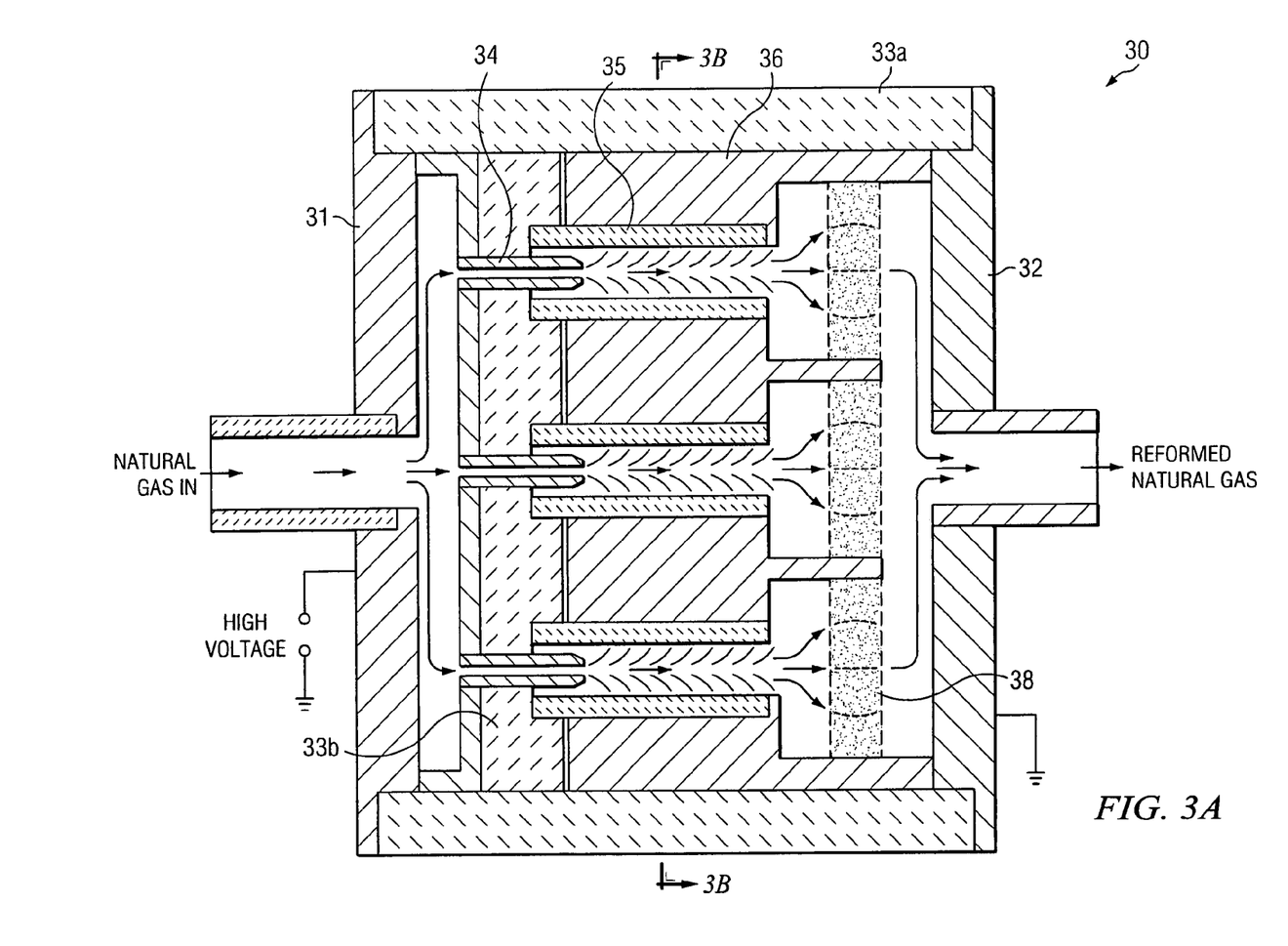
FIGS. 3A and 3B illustrate a second embodiment of nonthermal plasma gas reforming chamber.
Figure 3B:
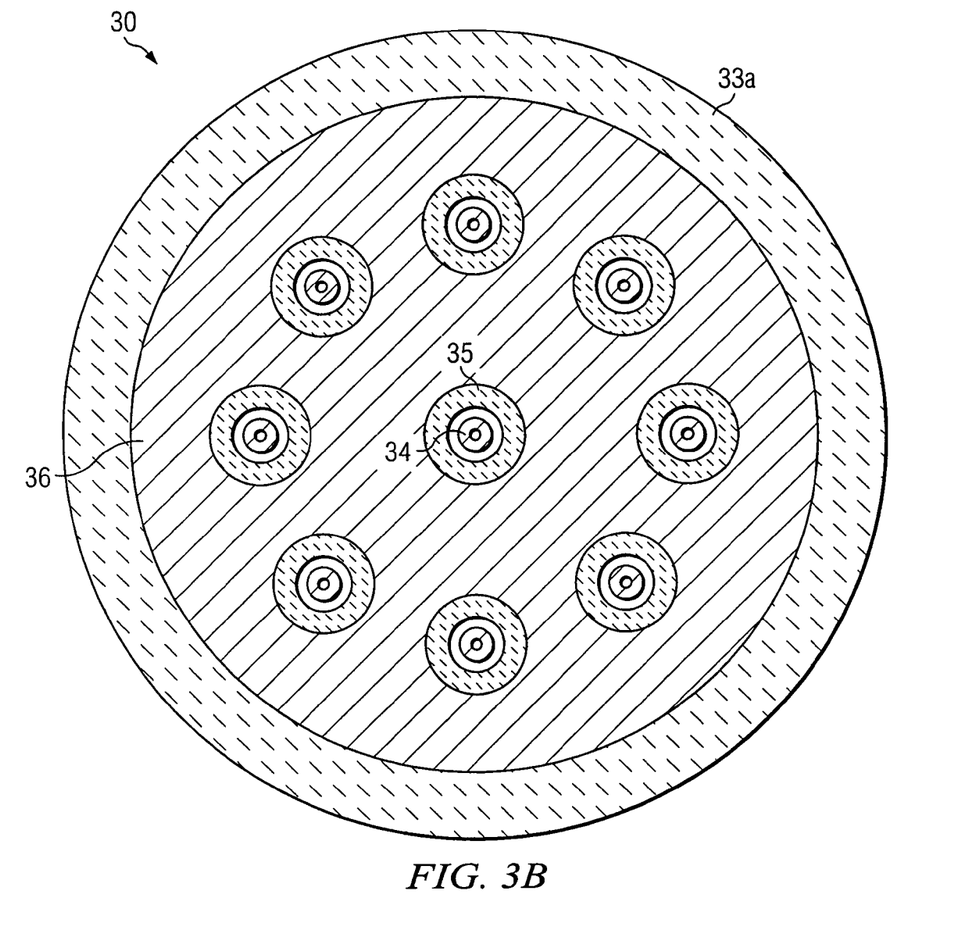

FIGS. 2, 3A, and 3B are diagrammatic sketches of two forms of nonthermal plasma discharge chambers designed to continuously ionize, dissociate, and reform the input natural gas in a flow-through manner. In both of these arrangements, the reformed gas at the exit of the plasma discharge chamber, which contains the reformed molecular nitrogen in the form of ammonia, is fed to a nondispersive infrared absorption sensor designed to quantitatively measure the ammonia content.

FIG. 2 illustrates a basic flow-through nonthermal plasma discharge chamber 20, intended to ionize and dissociate and reform the natural gas passing through it. The embodiment of FIG. 2 consists of axially symmetric metallic gas inlet end 21 and metallic gas outlet end 22, separated and insulated by a nonconducting cylindrical housing 23 and a nonconducting disk 23b across the cross section of housing 23.

Natural gas entering the chamber 20 is confined to flow through a narrow capillary nozzle 24 to which is applied, via the metallic inlet end 21, an electrical potential sufficiently high to produce an energetic corona discharge at the sharp outlet tip of the nozzle 24. The nozzle extends into a relatively thin-wall tubular ceramic dielectric sleeve 25 having a slightly larger inside diameter than the outside diameter of the nozzle 24. In turn, this dielectric sleeve 25 is contained in a cylindrical metallic block 26 which is at ground potential via the metallic structure of the gas outlet end 22 of the chamber 20. An example of a suitable material for the nonconducting elements (housing 23a, disk 23b, and sleeve 25) is a ceramic material.

The corona discharge in the immediate vicinity of the nozzle tip forms a plasma zone through which all of the gas exiting the nozzle 24 must pass, resulting in an efficient and essentially complete ionization and dissociation of the throughput gas. The electric field emanating from the tip of the nozzle 24 diverges radially about the axis of the chamber toward the dielectric sleeve 25 and its externally surrounding grounded metallic block 26. The dielectric sleeve 25 acts as an insulating barrier to prevent any thermal arc discharges between the nozzle 24 and the grounded block 26. The ionized gas molecules and dissociated gas atoms and molecular radicals are dispersed along trajectories governed by the vector sum of the axial gas flow velocity and the radial electrostatic mobility of the charged gas atoms and molecules in the electric field to fill the cross-section of the sleeve 25.

The energy density in the nozzle-tip plasma discharge zone is made sufficiently high by adjusting the electrical potential applied to the nozzle 24, such that certain chemical reactions can take place among the various dissociated gas components and thereby reform the original gas constituents into other compounds. The energy density of the plasma zone diminishes with distance downstream of the nozzle 24, allowing the reforming reactions to stabilize through the cooling effects of the gas transport flow. The reformed gas exits the confining flow path of the sleeve 25, and enters a diffusion plenum containing a labyrinth of grounded wire-mesh screens 28 (or other porous grounded metallic obstacles) by which any remaining ions are neutralized prior to leaving the chamber 20.

The flow rate through the plasma discharge chamber 20 is typically low, on the order of 0.5 liter/minute. The flow-confining capillary nozzle 24 and sleeve 25 are properly sized with regard to the throughput flow rate to achieve laminar gas flow conditions through the chamber 20.

Upon exiting the plasma discharge chamber 20, the reformed gas flows through a nondispersive infrared absorption sensor 200, where the amount of ammonia is selectively measured. This measurement is feasible because the infrared absorption bands of ammonia are distinctly separated from those of the hydrocarbon constituents of natural gas and carbon dioxide as well as the various new compounds that might occur as a result of the gas reforming process. In particular, ammonia has its strongest absorption band at a wavelength peak of 10.74 μm with a second nearby absorption band at a wavelength peak of 10.34 μm. By sensing the amount of ammonia in the reformed gas in a quantitative and calibrated way using infrared absorption, say, in the 10.74 μm wavelength band, the ammonia measurement may be accurately correlated with the original amount of molecular nitrogen in the natural gas.

The correlation between the measured amount of ammonia and the original amount of nitrogen is governed largely by the experimental performance of the plasma discharge chamber 20 and the inherent chemical reforming pathways that can occur in typical mixtures of natural gas. The various parameters of the plasma discharge and the physical geometry of the capillary nozzle and other discharge components, including the magnitude, time dependence, and polarity of the voltage applied to the nozzle, may be adjusted and optimized in combination to yield the maximum practical amount of ammonia, with the goal of transforming all of the original nitrogen to ammonia. By attaining this goal, the measured ammonia content of the reformed gas will be directly indicative of the original nitrogen content in the natural gas.

The rate at which the ammonia measurements can be updated is governed by the time required for the infrared absorption measurement to be updated since the gas reforming process occurs on a continuous flow-through basis. Therefore, in keeping with the normal performance capabilities of conventional nondispersive infrared gas sensors, the refresh rate of ammonia measurements may be as frequent as once every 15–20 seconds, depending on the volumetric gas turn-over time and signal averaging required within the infrared sensor. In practice, the updated analog output measurements of ammonia from the infrared sensor will be digitized and transferred to an auxiliary data acquisition and processing system where they are analyzed to determine the amount of molecular nitrogen originally present in the natural gas.

FIGS. 3A and 3B illustrate a multiple-channel plasma discharge chamber 30, having multiple nozzles 34. Using chamber 30, the throughput gas either may be reformed at a higher volumetric flow rate or the capillary nozzles made smaller to enhance the corona discharges at each nozzle tip without exceeding laminar gas flow through the chamber.

As an example, the inlet end 31 of chamber 30 has nine narrow capillary nozzles 34, which are similar to the nozzle 24 of FIG. 2, symmetrically oriented around the axis of chamber 30. By using nine capillary nozzles 24 having a flow-through cross-sectional area one-half as large as the single nozzle illustrated in FIG. 2, the total throughput gas flow rate will be increased by a factor of 9/2=4.5.

In other respects, chamber 30 is similar in structure and function to chamber 20. The reformed gas combines to exit in a common stream to exit at outlet end 32. A nonconducting sleeve 35 receives gas from each nozzle, and the sleeves are embedded in a metallic block 36. The chamber has a nonconductive housing 33a and disk 33b like those of chamber 20.

Reforming the Gas to Create Molecular Ions

In a second embodiment, the first step is a direct excitation-dissociation-formation process. Direct excitation and dissociation of molecular nitrogen may be effected through a process by which highly excited states of the nitrogen molecular ion ($N_2^+$) are formed subsequent to impact by energetic electrons. A fraction of the diatomic molecular ions that result may be sufficiently excited to dissociate or recombine to form the triatomic molecular ion ($N_3^+$). The second step is a quantitative measurement of nitrogen molecular ions.

For the second embodiment of this invention, the energy source is an intense field of energetic electrons to produce by electron bombardment of $N_2$ nearly-dissociated, excited states of the diatomic molecular ion ($N_2^+$). Collisions of these highly excited diatomic molecular ions with neutral molecular nitrogen yield the triatomic molecular ion ($N_3^+$) and atomic nitrogen, the reaction being slightly endothermic ($\Delta H°_o$=4.97 eV). The intense electron field is readily obtained from a β-emitting radioisotope, such as $^{63}$Ni or carbon-14, wherein the emitter substrate on which the radioisotope is deposited is fixed at a bias potential. Therefore, direct measurement and quantization of molecular nitrogen is accomplished by forming symmetry species of the molecular ions that enable infrared-active vibrational transitions. Non-dispersive infrared absorption is again useful in detecting such transitions.

Molecular ions of nitrogen for direct infrared absorption measurement of the symmetry-allowed molecular-ion species are generated in an intense energy field through electron bombardment of the neutral molecular nitrogen with an β-emitting radioisotope. The symmetry-allowed molecular species of nitrogen are those whose symmetry properties of the corresponding molecular-electronic state permit infrared-active vibrational transitions. In this embodiment of the present invention, electron bombardment of the molecular nitrogen constituent of the gas volume is used to generate a reactive manifold wherein spontaneous collisions of the highly excited (near dissociation threshold) molecular ions with molecular nitrogen (neutrals) yield dissociation of the molecular species and subsequent formation of highly excited states of triatomic molecular ion species of nitrogen.

The molecular ion-generating reaction may take place in a plasma chemistry reactor through which samples of natural gas flow, and the nitrogen constituent of the gas mixture is ionized, dissociated, and reformed into new triatomic molecular ion species. One mechanism for this reaction follows:

In the foregoing mechanism, parameters such as occupancy of specific electronic states of the molecular ion, the Franck-Condon factors for neutralization transitions, the probability of dissociation as a function of the ion energy, and the reaction cross-section to produce a specific product all play important, if not deterministic, roles in promoting the reaction. In particular, neutralization of the molecular ion with a nearby non-conducting, semi-conducting, or conducting surface—resonant or Auger neutralization channels—encumbers this reaction by affecting the lifetime of the excited molecular ions.

Figure 4:
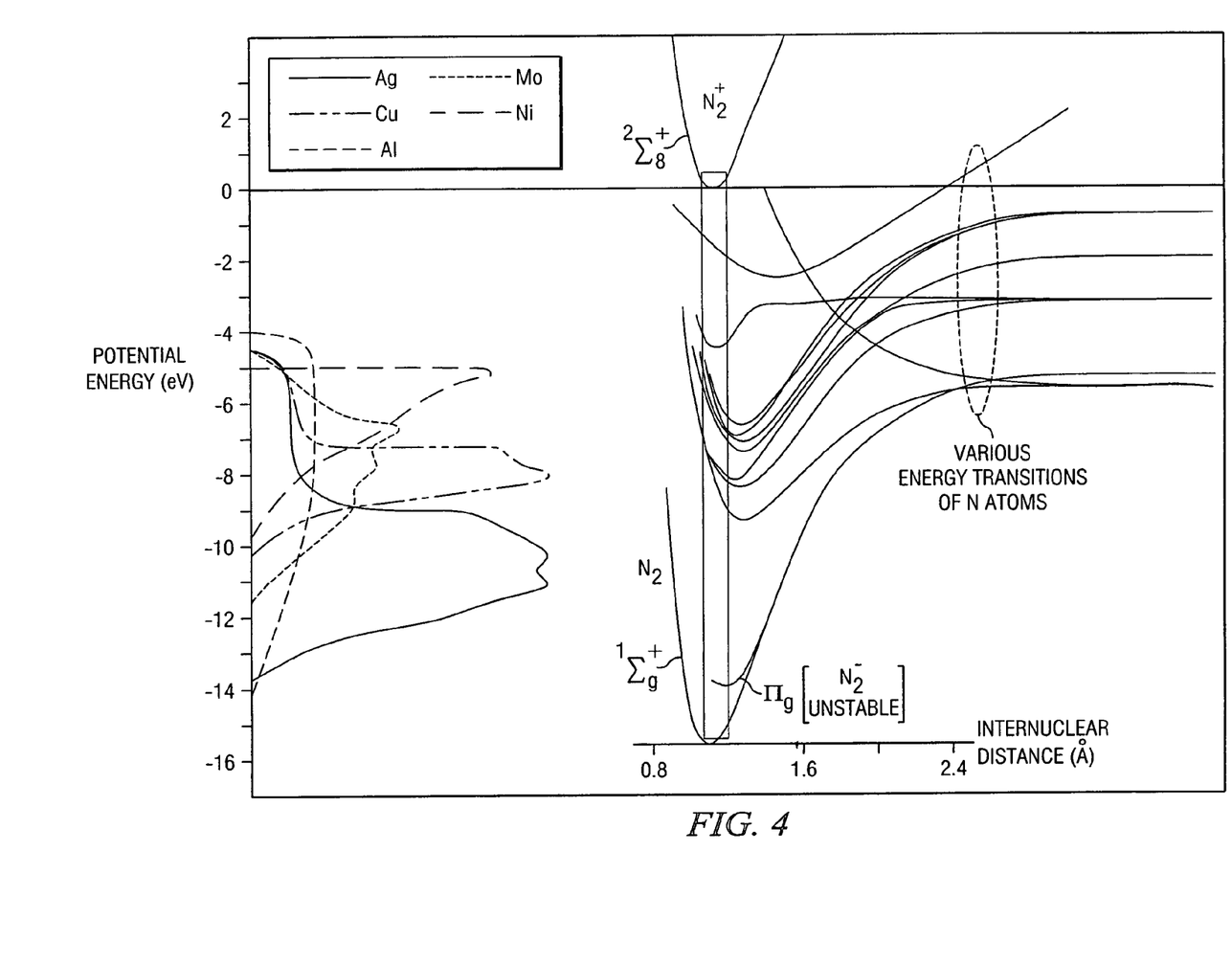
FIG. 4 is a set of electron energy level diagrams representing available transitions for molecular nitrogen and the molecular ion states.

FIG. 4 is a set of molecular-electronic energy level diagrams representing, in part, the excited states of the diatomic molecular ion and the available manifold of transitions. The relationship between the available manifold of transitions for source excited-species, the diatomic molecular ion, and the electronic band structure of some metals is also shown. The electronic band structures for several metals are also shown. Because the triatomic molecular ion in all of its molecular electronic states can undergo vibrational transitions that are infrared-active, non-dispersive infrared absorption is a convenient method of detecting this species.

Figure 5:
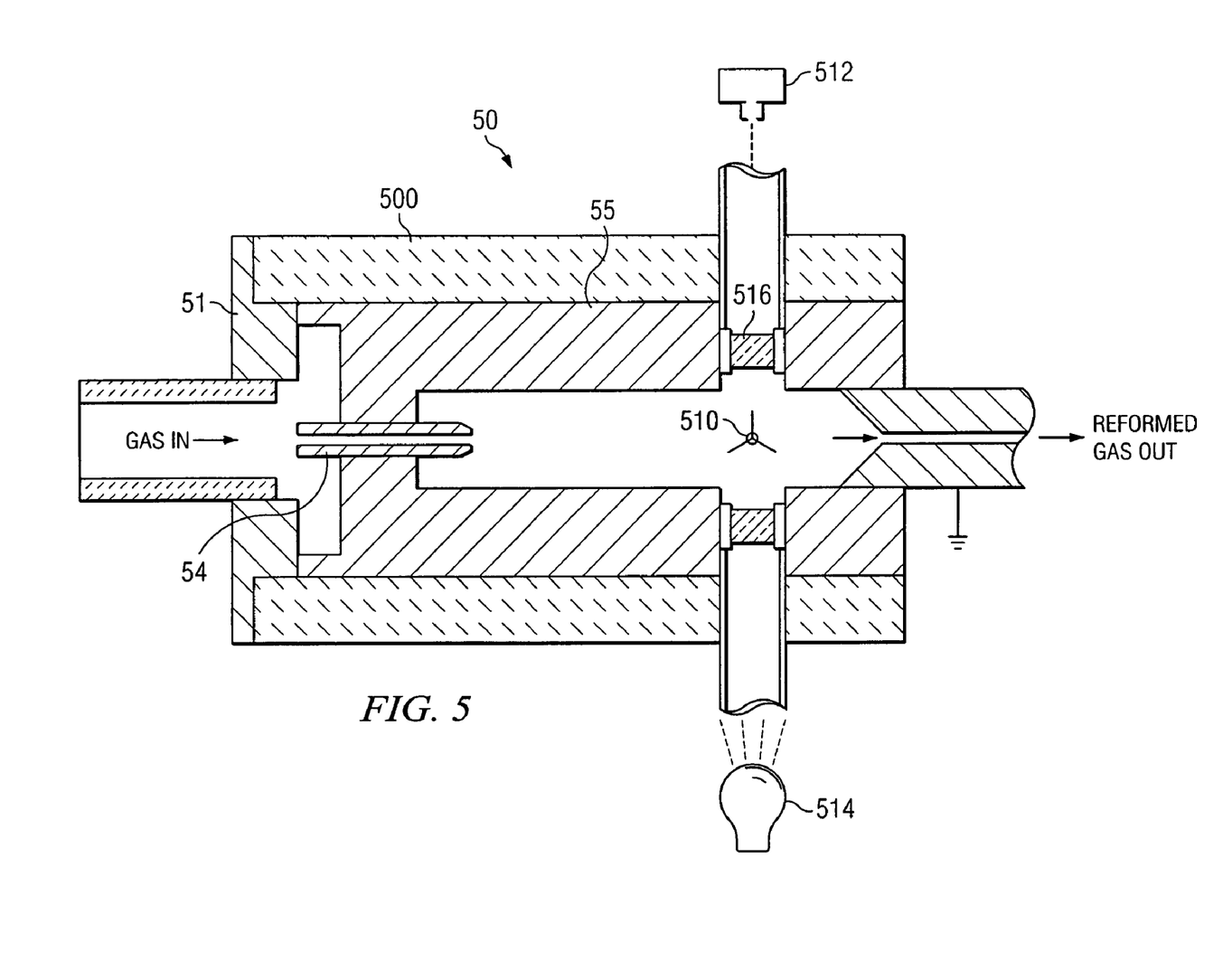
FIG. 5 illustrates a reaction chamber for the non-dispersive infrared absorbance detection of nitrogen molecular ions.

FIG. 5 is a schematic of a flow-through capillary reaction chamber 50, useful in determining the concentration of molecular nitrogen from a natural gas source by generating the molecular ions of the above-described reaction. Various structural elements of reactor 50 are similar to those of reactor 20. A capillary nozzle 54 emits gas into an interior chamber of the reactor. Gas enters through an inlet in end cap 51. The reactor has an interior cylindrical sleeve 55 and an external housing 500.

For reactor 50, a $^{63}$Ni source (β-emitter) 510 is used to effect electron bombardment of the gas stream in the beam path of a non-dispersive infrared detector 512, where the triatomic molecular ion of nitrogen is detected in its vibrationally hot state. An infrared source 514 is also illustrated, as well as transmitting windows 516 that permit the infrared beam to intersect the gas flow.

Advantages

The methods of determining the amount of molecular nitrogen in natural gas described above have several advantages over previously known methods. Both method provide for on-line quantitative determination of nitrogen in natural gas, and perhaps in various other gas mixtures. Indeed, with the exception of gas chromatograph techniques, there are no present-day sensors or established sensing methods for selectively determining the diluent nitrogen content in natural gas.

Furthermore, the narrow capillary plasma discharge nozzle confined within a small-diameter dielectric sleeve as described in this invention provides an effective means of ionizing and reforming essentially all of the natural gas flowing through the plasma discharge chamber. This feature provides an accurate and direct basis for correlating the amount of measured ammonia in the reformed gas with the actual amount of molecular nitrogen in the input natural gas. The confined capillary flow paths incorporated in the reforming process permit the nitrogen determination process to operate continuously as an automated on-line measurement method.

The invention claimed is:

1. A method of determining the original amount of nitrogen in a gas mixture, the mixture also containing a least one hydrocarbon constituent, comprising ionizing the gas mixture, by introducing energy into the gas by subjecting the gas to a nonthermal plasma discharge;

controlling the amount of energy introduced into the gas, such that nitrogen atoms in the gas and hydrogen atoms from at least one hydrocarbon constituent of the gas are dissociated and reform to ammonia;

wherein the energy is sufficient for dissociation of the nitrogen but insufficient for dissociation of methyl;

measuring the amount of ammonia in the gas;

wherein the ionizing and controlling steps are performed by routing the gas mixture through a nonthermal plasma discharge chamber, and wherein the measuring step is performed by subsequently routing the gas into a nondispersive infrared absorption detection chamber; and estimating the original amount of nitrogen in the gas mixture, based on the amount of ammonia measured in the preceding step.

2. The method of claim 1, wherein the gas mixture is a natural gas mixture.

3. The method of claim 1, wherein the hydrocarbon constituent is methane.

4. The method of claim 1, wherein the energy is controlled such that it is insufficient to ionize constituents having higher bond strength than that of nitrogen.

5. The method of claim 1, wherein the measuring step is performed using infrared absorption techniques.

6. The method of claim 5, wherein the infrared absorption is performed at a wavelength of 10.34 micrometers.

7. The method of claim 5, wherein the infrared absorption is performed at a wavelength of 10.74 micrometers.

8. The method of claim 1, further comprising the steps of repeating all steps for successive samples of the gas mixture.

9. The method of claim 8, wherein the repeating steps are consistent with each other.

10. The method of claim 1, wherein the estimating step is performed by correlation of the measured amount of ammonia to the original amount of nitrogen in the gas.

11. The method of claim 1, wherein the controlling step is performed such that substantially all of the nitrogen is reformed into ammonia.

* * * * *